(12) United States Patent
Meckler et al.

(10) Patent No.: US 9,278,904 B2
(45) Date of Patent: *Mar. 8, 2016

(54) SYNTHESIS OF CHIRAL AMPHETAMINE DERIVATIVES BY STEREOSPECIFIC, REGIOSELECTIVE CUPRATE ADDITION REACTION WITH AZIRIDINE PHOSPHORAMIDATE COMPOUNDS

(71) Applicant: Chemapotheca, LLC, Delmar, NY (US)

(72) Inventors: Harold Meckler, Delmar, NY (US); Brian Thomas Gregg, Altamont, NY (US); Jie Yang, Rensselaer, NY (US)

(73) Assignee: Chemapotheca, LLC, Delmar, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/189,630

(22) Filed: Feb. 25, 2014

(65) Prior Publication Data

US 2015/0183716 A1 Jul. 2, 2015

Related U.S. Application Data

(60) Provisional application No. 61/922,729, filed on Dec. 31, 2013.

(51) Int. Cl.
| | | |
|---|---|---|
| *C07C 209/68* | (2006.01) | |
| *C07F 9/564* | (2006.01) | |
| *C07C 209/62* | (2006.01) | |
| *C07F 9/24* | (2006.01) | |

(52) U.S. Cl.
CPC .............. *C07C 209/62* (2013.01); *C07F 9/2458* (2013.01); *C07F 9/2475* (2013.01); *C07B 2200/07* (2013.01); *C07F 9/564* (2013.01)

(58) Field of Classification Search
None
See application file for complete search history.

(56) References Cited

U.S. PATENT DOCUMENTS

| 6,399,828 B1 | 6/2002 | Boswell |
| 7,705,184 B2 | 4/2010 | Buenger |
| 8,487,134 B2 | 7/2013 | Meudt |

FOREIGN PATENT DOCUMENTS

FR          5.857 M      3/1968

OTHER PUBLICATIONS

CAPLUS printout of "Veitia et al., Synthesis of novel N-protected beta3-amino nitriles: study of their hydrolysis involving a nitrilase-catalyzed step. Tetrahedron: Assymetry. 2009, 20, 2077-2089."*
Moore et al., An efficient and operationally convenient gerenal synthesis of tertiary amines by direct alkylation of secondary amines with alkyl halides in the presence of Huenig's base. Arkivoc. 2005, 287-292.*

Crossland et al., A Facile Synthesis of Methanesulfonate Esters. Journal of Organic Chemistry. 1970, 35, 3195-3196.*
Rydzewski, Real World Drug Discovery 2008, 42-43.*
L.A. Cates, et al., "Phosphorus-Nitrogen Compounds VI: Some Phenethylamine Derivatives," *Journal of Pharmaceutical Sciences*, vol. 55, No. 12, Dec. 1966, pp. 1400-1405.
T. Gajda, et al., "Synthesis of Primary *sec*-Alkylamines via Nucleophilic Ring-opening of N-Phosphorylated Aziridines," *Tetrahedron*, vol. 53, No. 13, 1997, pp. 4935-4946.
K. Osowska-Pacewicka, et al., Reactions of N-Phosphorylated Aziridines with Dianions Derived from Ethyl Acetoacetate and 1,3-Diketones: New Route to Substituted Pyrrolines and Pyrrolidines, *Synthetic Communications: An International Journal for Rapid Communication of Synthetic Organic Chemistry*, vol. 28, No. 7, 1998, pp. 1127-1137.
P. Giles, et al. "An Improved Process for the *N*-Alkylation of Indoles Using Chiral *N*-Protected 2-Methylaziridines," *Organic Process Research & Development*, vol. 7, No. 1, 2003, pp. 22-24.
A. Poshkus, et al., "The Reaction of Neutral Esters of Trivalent Phosphorus Acids with Inorganic Acid Chlorides. I. The Reaction of Trialkyl Phosphites with Sulfuryl Chloride," *Journal of the American Chemical Society*, Contribution from the Research and Development Center of the Armstrong Cork Co., 1957, pp. 6127-6129.
A. Bořkovec, et al., Insect Chemosterilants. III. 1-Aziridinylphosphine Oxides, *Journal of Medicinal Chemistry*, vol. 9, Jul. 1966, pp. 522-526.
N. Stojanovska, et al., "A Review of Impurity Profiling and Synthetic Route of Manufacture of Methylamphetamine, 3,4-methylenedioxymethylamphetamine, amphetamine, dimethylamphetamine and *p*-methoxyamphetamine," *Forensic Science International*, vol. 224, 2013, pp. 8-26.
M. Sylla-Iyarreta Veitia, et al., "Synthesis of Novel N-Protected β3-Amino Nitriles: Study of Their Hydrolysis Involving a Nitrilase-Catalyzed Step," *Tetrahedron: Asymmetry*, vol. 20, No. 18, 2009, pp. 2077-2089.
Zwierzak, Andrzej, Alkylation of Diethyl Phosphoramidates—A Simple Route from Primary to Secondary Amines, Angew Chem Intl Ed Engl 16 (1977) No. 2 p. 107.
WO 2015/130660 Int'l Search Report—Zwierzak, Synthesis Comm., Phosphor-amido-mercuration, pp. 918, Nov. 1982; Zwierzak, Tetrahedron Letters, Synthesis of Primary sec-Alkylamines, 53:13, 4935, 1997; and Li Xinyao, Synthesis, An Improved and Mild Wenker Synthesis of Aziridines, vol. 20, 3423, 2010, abstract, scheme 2, Jun. 25, 2015, Chemapotheca.
WO 2015/130660 Int'l Written Opinion of '660 ISR, Jun. 25, 2015, Chemapotheca.

(Continued)

*Primary Examiner* — Rebecca Anderson
*Assistant Examiner* — Po-Chih Chen
(74) *Attorney, Agent, or Firm* — Todd L. Juneau

(57) ABSTRACT

The invention includes processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursors using an organometallic compound such as a copper salt, where the novel aryl or aryl-alkyl phosphoramidate precursor is then easily converted to the target compounds using known reactions.

20 Claims, No Drawings

(56) References Cited

OTHER PUBLICATIONS

WO 2015-130661 Int'l Search Report—Zwierzak, Synthesis Comm., Phosphor-amido-mercuration, pp. 918, Nov. 1982; Aeseng, PhD Thesis, Asymmetric Synthesis of 2-Substituted-Aminotetralins, Norway Univ Sci Tech, Nov. 2010, Scheme 1,4; and Li Xinyao, Synthesis, An Improved and Mild Wenker Synthesis of Aziridines, vol. 20, 3423, 2010, abstract, scheme 2, Jun. 25, 2015, Chemapotheca.
WO 2015/130661 Int'l Written Opinion of '661 ISR, Jun. 29, 2015, Chemapotheca.
Kojima, Scifinder CAS Registry 1485-13-8 for 2-methyl-3-phenyl-aziridine, Kojima 1959 et al.
Streuff—Aziridines—Overview and Recent Advancements, Stoltzgroup Literature Seminar, Jan. 26, 2009.
Allen and Ely, Synthetic Methods for Amphetamines, Crime Scene magazine, p. 15-25 Spring 2011.
Mekenyan, Scifinder 2010:1165579 ACS, Aziridine Use of Genotoxicity Information . . . , Chem Res Tox vol. 23 Issue 10 pp. 1519-1540, 2010.
Sakurai, Scifinder 2000-630740 ACS, Aziridine Recommendation of Occupational exposure limits, J Occup Health, vol. 42, Issue 4, pp. 213-228, 2000.
Koleva, Scifinder 2011-1058228 ACS, Modelling of Acute Oral . . . aziridine toxicity, Toxicology In Vitro, vol. 25, Issue 7, pp. 1281-1293, 2011.
Lambrechts, Leuckart-specific impurities in amphetamine, Bulletin on Narcotics, UNODC Everywhere, pp. 47-57, Jan. 1, 1984.
D'Ambra, Scifinder Search Results for D'Ambra patents (allergy drugs, regioselectivity) Accession 2002-52000, from US20020007068, 1999.
Rege et al. Drug Metabolism and Disposition, vol. 30 No. 12, pp. 1337-1343, Irreversible Inhibition of CYP2D6 by (−) Chloroephedrine (impurity), 2002.
Emea Committee for Medical Products, Grignard Solvents Committee, Feb. 10, 2005, pp. 1-7.
FDA CDER Guidance for Industry, (genotox guidance) Dec. 2008.
Skinner, Methamphetamine Synthesis via Hydriodic . . . , Forensic Sci Int'l, 48 (1990) 123-134, red phos method.
Anderson, Development of a Harmonized Method for Profiling . . . , Forensic Sci Int'l 169 (2007) pp. 50-63, GC method.
Power, An Unusual Presentation of Customs Seizure, Forensic Sci Int'l 234 (2014) e10-e13.
Barker, A Study of the Use of Ephedra, Forensic Sci Int'l 166 (2007) 102-109.
Humphrey, Keeping Afloat in a Sea of Impurities, Global Safety Assessment, Astra Zeneca Jul. 6, 2007.
EMEA Solvent (Grignard) impurities, ICH Topic Q3C (R4), pp. 1-22, 2010.
Funel and Abele, Diels Alder Reactions Part 1, Angewandte Reviews, Angew. Chem Int 2013 vol. 52, 1-44, 2013.
Funel and Abele, Diels Alder Reactions Part 3, Angewandte Reviews, Angew. Chem Int 2013 vol. 52, 1-44, 2013.
Funel and Abele, Diels Alder Reactions Part 2, Angewandte Reviews, Angew. Chem Int 2013 vol. 52, 1-44, 2013.
Funel and Abele, Diels Alder Reactions Part 4, Angewandte Reviews, Angew. Chem Int 2013 vol. 52, 1-44, 2013.
Stephens, Substituted Aziridines, Prep and Properties, J Chem Engin, vol. 8, No. 4, pp. 625-626, Oct. 1963.
Stephens, Relative rates of Reaction and Direction of Ring Opening, J Chem Engin, vol. 14, No. 1, pp. 114-115, Jan. 1969.
Hata, Fragmentation Reaction of Ylide, JACS vol. 98-19, pp. 6033-6036, Sep. 1976.
Jessing, Aziridines in Synthesis, Baran Lab Jan. 2007.
Hassner, A.; Galle, J. E.; "Ring Opening of Aziridine Phosphonates. Correlation of Structure, Nuclear Magnetic Resonance Spectra and Reactivity" *J. Org. Chem.*, 1976, 41, 2273-2276.
Stromberg, Comparative GC Analysis, J Chromatography 106 (1975) 335-342, amphet sulfate.
Lambrechts, Profiling of Impurities in Illicit Amphetamine, 1986 J Chromatography vol. 369 (1976) pp. 365-377 HPLC impurities.
Allen, Methamphetamines from Ephedrine, J Forensic Sci vol. 32, No. 4, Jul. 1987, pp. 953-962.
Milstein, Friedel Crafts Reactions of Htree Member Heterocycles, J Het Chem vol. 5, pp. 339-241, Mar. 1968.
Hassner, Regiospecificity: A Useful Terminology, JOC vol. 33, No. 7 pp. 2684-2686 Jul. 1968.
Todd, Aneurin, A Synthesis of Thiochrome, J Chem Soc 1936, pp. 1601-1605.
Hider, Prep of Evidence in Amphet Prosecutions, J Forensic Sci pp. 75-79 1960's.
Anandasankar, Scifinder 7763-71-5, referring to WO 2011 130726, priority to US 2011-32804, and 2010-61325236, 2010.
Osowska-Pacewicka, N-Phosphorylated Aziridines—new reagents for electrophilic amination, Polish J Chem 68-6 pp. 1263-1264 1994.
Pramanik, An Efficient Scalable Process for Benzphetamine HCI, JACS J Org Process Res Dev 2014 vol. 18 pp. 495-500.
Snodin, Potentially Mutagenic Impurities, J Org Process Res Dev 2014, vol. 18, pp. 836-839 Racemic.
Raman, Regulatory Expectations Towards Genotoxic, J Org Process Res Dev 2014 vol. 18 pp. 834-835.
Teasdale, Regulatory Highlights, J Org Process Res Dev 2014 vol. 18, 458-472.
Jawahar, Direct Stereospecific Synthesis of Unprotected N—H and N-Me Aziridines from Olefins, Sciences 343, 61 pp. 61-65, 2014.
Koziara, A.; Oleiniczak, B.; Osowska, K.; Zwierzak, A. "Phosphoramidomercuration-Demercuration: A Simple Two-Step Conversion of Alkenes into Alkanamines" *Synthesis* 1982, 918-920.

\* cited by examiner

SYNTHESIS OF CHIRAL AMPHETAMINE DERIVATIVES BY STEREOSPECIFIC, REGIOSELECTIVE CUPRATE ADDITION REACTION WITH AZIRIDINE PHOSPHORAMIDATE COMPOUNDS

CROSS-REFERENCE TO RELATED APPLICATIONS

None.

STATEMENT REGARDING FEDERALLY SPONSORED RESEARCH

No federal government funds were used in the research or development of this invention.

NAMES OF PARTIES TO A JOINT RESEARCH AGREEMENT

None.

REFERENCE TO A SEQUENCE LISTING

None.

BACKGROUND

1. Field of the Invention

This is invention is related to processes for synthesis of amphetamine derivatives and novel intermediates thereby.

2. Background of the Invention

The commercial importance of amphetamine derivatives has led to the development of numerous synthetic methods for their synthesis and their derivatization. One problem with amphetamine synthesis is that amphetamines have a stereo-defined amine center, which can be subject to racemization. Accordingly, only stereospecific methods are useful. However, stereospecific methods do not provide the economic requirements of high yields, high selectivity and low process costs. Typically such reactions involve a coupling agent, such as Grignard or organolithium reagents. Conventional teaching requires that the use such organometallics requires that the reaction temperature be maintained at a cold temperature, such as an ice bath at less than 10 degrees Celsius.

Another problem with amphetamine synthesis is that the intermediates are toxic as well as flammable. This requires special handling such as double-walled drums and safety accommodations to protect manufacturing personnel.

The prior art in U.S. Pat. No. 6,399,828 teaches the production of amphetamine using various methods. In one approach norephedrine is refluxed with hydrogen iodide and red phosphorous. In another approach norephedrine is chlorinated using thionyl chloride and then catalytically hydrogenated. In U.S. Pat. No. 7,705,184, amphetamine synthesis is disclosed using hydrogenation of a chlorinated phenylpropanolamine. Aziridine chemistry, and specifically aziridine phosphoramidates are not taught in the amphetamine synthesis prior art.

Zwierzak et al. disclose a method of reacting N-phosphorylated aziridines with copper-modified Grignard reagents as a new route to substituted pyrrolines and pyrrolidines. However, Zwierzak et al discloses this method as being regiospecific, which it is not. Int'l J. for Rapid Commun. of Syn. Org. Chem., 28:7, 1127-1137 (1998). Accordingly, where the prior art contained an erroneous teaching, it was surprising to discover otherwise.

Additionally, the use of protecting groups and leaving groups is well known. However, it has been discovered that there is significant variation among the various protecting groups. Specifically, where a carbonyl is used as a protecting group, the reaction must be kept at below −10 degrees Celsius or the carbonyl will react with the Grignard reagent. Where a sulfonyl is used as a protecting group, it is impossible to remove the protecting group without destroying the molecule.

Accordingly, there is a need for synthetic processes and useful compounds for the manufacture of amphetamine and its derivatives which have high chemical yield, high selectivity, low cost, lower toxicity and are less dangerous to handle.

BRIEF SUMMARY OF THE INVENTION

The present invention addresses one or more of the shortcomings of the prior art by providing processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursors using a modified organometallic compound such as a organocopper reagent, where the novel aryl or aryl-alkyl phosphoramidate precursor is then easily converted to the target compounds using known reactions, e.g. acidification, methylation of the nitrogen followed by dephosphorylation, etc.

In one preferred aspect the invention provides a synthetic pathway to amphetamine derivatives using an aziridine based process with an organometallic compound by heating the reactants in a first step, and then adding as a second step the Grignard reagent in a dosage controlled fashion. In a preferred embodiment, the reaction is heated to above 40 degrees C., preferably above about 45 degrees C., and more preferably above about 48 degrees C. In one embodiment, the temperature is maintained from 48-51 deg. C. for about 30 minutes and then brought to room temperature.

In another preferred embodiment, the invention provides a process of making the dexamphetamine, said process comprising:

providing a compound of Formula 5:

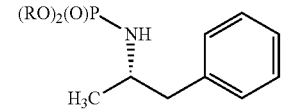

wherein R is alkyl or aryl; and
deprotecting the compound of Formula 5 under acidic conditions effective to produce dexamphetamine of Formula 1:

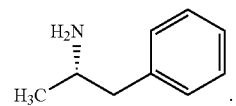

In preferred aspects, the dexamphetamine process comprises wherein the acidic conditions are aqueous hydrochloric, sulfuric or phosphoric acids.

In preferred aspects, the dexamphetamine process comprises wherein the aqueous acid water content is in an amount of 50% to 90%

In preferred aspects, the dexamphetamine process comprises wherein the R=methyl, ethyl, isopropyl or phenyl.

In preferred aspects, the dexamphetamine process comprises wherein said providing a compound of Formula 5 comprises:

providing a compound of Formula 4:

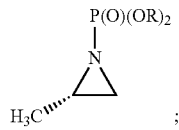

wherein R is alkyl or aryl and reacting the compound of Formula 4 with phenylmagnesium halide and a copper halide catalyst under solvent and temperature conditions effective to produce a compound of Formula 5 in a purity substantially free of any regioisomeric impurities.

In preferred aspects, the dexamphetamine process comprises wherein the regioisomeric purity of Formula 5 is >99% and the regioisomer is >0.1%.

In preferred aspects, the dexamphetamine process comprises wherein the R=methyl, ethyl, isopropyl or phenyl.

In preferred aspects, the dexamphetamine process comprises wherein the copper halide catalyst is CuCl, $CuCl_2$, CuBr or Copper nanoparticles.

In preferred aspects, the dexamphetamine process comprises wherein the solvent is an organic ether.

In preferred aspects, the dexamphetamine process comprises wherein the solvent is tetrahydrofuran or 2-methyltetrahydrofuran.

In preferred aspects, the dexamphetamine process comprises wherein said treating is carried out at a temperature of from about −10° C. to about 70° C.

In preferred aspects, the dexamphetamine process comprises wherein said treating is carried out at a temperature of from about 30° C. to about 60° C.

In preferred aspects, the dexamphetamine process comprises wherein said providing a compound of Formula 4 comprises:

providing a compound of Formula 3:

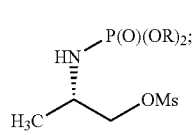

wherein R is alkyl or aryl; and reacting the compound of Formula 3 with the base under conditions effective to produce a compound of Formula 4.

In preferred aspects, the dexamphetamine process involving Formula 3 comprises a compound of Formula 3 wherein the R=methyl, ethyl, isopropyl or phenyl.

In preferred aspects, the dexamphetamine process comprises wherein the base is potassium hydroxide or potassium carbonate.

In preferred aspects, the dexamphetamine process comprises wherein said providing a compound of Formula 3 comprises:

providing a compound of Formula 2:

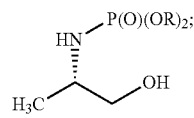

wherein R is alkyl or aryl; and reacting the compound of Formula 2 with methanesulfonyl chloride and a base under conditions effective to produce a compound of Formula 3.

In preferred aspects, the dexamphetamine process comprises a compound of Formula 2 wherein the R=methyl, ethyl, isopropyl or phenyl.

In preferred aspects, the dexamphetamine process comprises wherein said providing a compound of Formula 2 comprises:

providing a compound of Formula 1:

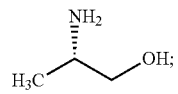

and reacting the compound of Formula II with the appropriate

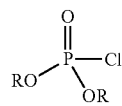

wherein R=alkyl or aryl under conditions effective to produce a compound of Formula 2.

In preferred aspects, the dexamphetamine process involving Formula 2 comprises wherein the R=methyl, ethyl, isopropyl or phenyl.

In another preferred embodiment, the invention provides a process of making the dex-N-methylamphetamine, said process comprising:

providing a compound of Formula 8:

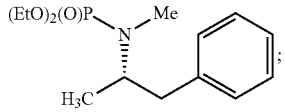

and deprotecting the compound of Formula 8 under acidic conditions effective to produce dex-N-methylamphetamine of Formula 9:

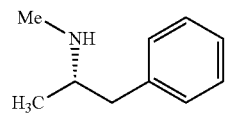

In preferred aspects, the dex-N-methylamphetamine process comprises wherein the acidic conditions are aqueous hydrochloric, sulfuric or phosphoric acids.

In preferred aspects, the dex-N-methylamphetamine process comprises wherein the aqueous acid water content is in an amount of 50% to 90%

In preferred aspects, the dex-N-methylamphetamine process comprises wherein said providing a compound of Formula 8 comprises:

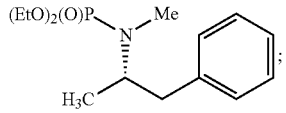

and reacting the compound of Formula 5b with a methyl alkylating agent and a base In another preferred embodiment, the invention provides a process of making the dex-N-ethylamphetamine, said process comprising:

providing a compound of Formula 10:

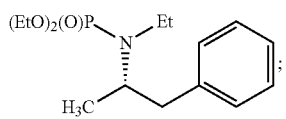

and deprotecting the compound of Formula 10 under acidic conditions effective to produce dex-N-ethylamphetamine of Formula 11:

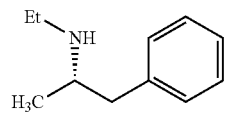

In preferred aspects, the dex-N-ethylamphetamine process comprises wherein the acidic conditions are aqueous hydrochloric, sulfuric or phosphoric acids.

In preferred aspects, the dex-N-ethylamphetamine process comprises wherein the aqueous acid water content is in an amount of 50% to 90%

In preferred aspects, the dex-N-ethylamphetamine process comprises wherein said providing a compound of Formula 10 comprises:

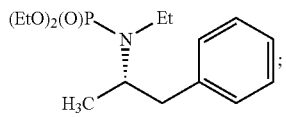

and reacting the compound of Formula 5b with a ethyl alkylating agent and a base In another preferred embodiment, the invention provides a compound of the formula:

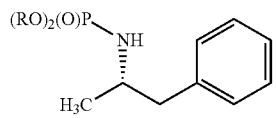

prepared according to one or more processes herein, in a regioisomeric purity of >1700:1
wherein:
R is alkyl or aryl In preferred aspects, the invention further comprises a compound of the formula:

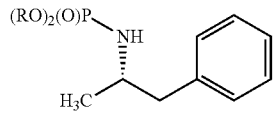

wherein the alkyl group is selected from the group consisting of methyl, ethyl or isopropyl In preferred aspects, the invention further comprises a compound of the formula:

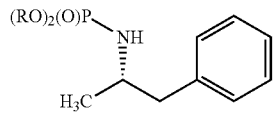

wherein the aryl group is phenyl.

In another preferred embodiment, the invention provides a compound of the formula:

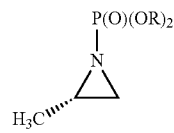

wherein: R is alkyl or aryl

In preferred aspects, the invention further comprises a compound of the formula:

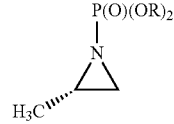

wherein the alkyl group is selected from the group consisting of methyl, ethyl or isopropyl.

In preferred aspects, the invention further comprises a compound of the formula:

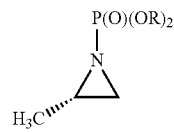

wherein the aryl group is phenyl.

In yet another preferred embodiment, there is provided a process for the synthesis of amphetamine derivatives comprising the step of performing a stereo-specific cuprate addition reaction upon an aziridine phosphoramidate compound to obtain a chiral aryl or aryl-alkyl phosphoramidate amphetamine precursor.

In yet another preferred embodiment, there is provided a process for solvent extraction of compounds 5a-d from a mixture of compounds 5a-d and 6a-d, comprising the step of performing a solvent extraction using a mixture of two or more solvents wherein at least one of the two or more solvents is THF.

DETAILED DESCRIPTION OF THE INVENTION

Accordingly, the present invention relates to processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursor using an organometallic compound such as a copper salt, where the novel aryl or aryl-alkyl phosphoramidate precursor is then easily converted to the target compounds using known reactions, e.g. acid dephosphorylation, methylation of the nitrogen followed by acid dephosphorylation, etc.

Alkyl means any C1-C10 straight or branched chain alkyl, wherein said alkyl, is optionally substituted with C1-C6 alkyl, C2-C6 alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl.

Aryl means any alicyclic or aromatic, mono-, bi- or tricyclic, carbo- or heterocyclic ring, wherein the ring is either unsubstituted or substituted with one or more substituent(s) independently selected from the group including, but not limited to, alkylamino, amido, amino, aminoalkyl, azo, benzyloxy, C1-C9 straight or branched chain alkyl, C1-C9 alkoxy, C2-C9 alkenyloxy, C2-C9 straight or branched chain alkenyl, C3-C8 cycloalkyl, C5-C7 cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties, including alicyclic and aromatic structures; wherein the individual ring size is 5-8 members; wherein said heterocyclic ring contains 1-6 heteroatom(s) independently selected from the group consisting of O, N, and S; and wherein said aromatic or tertiary alkyl amine is optionally oxidized. Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

R may also be in certain preferred embodiments any C2-C10 straight or branched chain alkenyl or C1-C10 alkoxy, unsubstituted or optionally substituted with moieties listed above.

Copper nanoparticles means particles having an average diameter of about 1 nm-100 nm.

Alkyl Phosphonic Acid Protecting group means any group attached to the aziridine nitrogen having one or more alkyl groups attached to a phosphorous atom thereby having the formula P—O—(OR)$_2$, where R1 and R2 can be the same or different, and include without limitation any alkyl, alkoxy or aryl group as defined herein, and including any and all equivalents thereof.

Solvents, as used and exemplified herein, are not intended to be limiting and may include without limitation solvents selected from Ligroine, Pentane, Hexane, Heptane, Octane, Cyclopentane, Cyclohexane, Cycloheptane, Cyclooctane, Dichloromethane, Chloroform, Carbon tetrachloride, 1,2-Dichloroethane, 1,1,2,2-Tetrachloroethane, Methylacetate, Ethylacetate, Propylacetate, Butylacetate, Dimethylformamide, Diethylformamide, Dimethylacetamide, Diethylacetamide, Diethylether, Diisopropylether, 20 methyl tert-Butyl ether, THF, Dioxane, Acetonitrile, Sulfolane, DMSO, HMPT, NMP or mixtures of these solvents. Preferred solvents are Dichloromethane, Chloroform, Ethyl acetate, Propyl acetate, Butyl acetate, Dimethylformamide, Diethylformamide, Dimethylacetamide, Diethylacetamide, Diisopropylether, methyl tert-Butyl ether, THF, Dioxane, Acetonitrile or mixtures of these. Especially preferred solvents are Dichloromethane, Chloroform, Ethyl acetate, Butyl acetate, Dimethylformamide, Dimethylacetamide, methyl tert-Butyl ether, THF, Dioxane, Acetonitrile or mixtures of these.

The term, regioselective or regioselectivity, means without limitation, by way of explanation, the preference of one direction of chemical bond making or breaking over all other possible directions. It can often apply to which of many possible positions a reagent will affect, such as which proton a strong base will abstract from an organic molecule, or where on a substituted benzene ring a further substituent will add. Because of the preference for the formation of one product over another, the reaction is selective. This reaction is regioselective because it selectively generates one constitutional isomer rather than the other.

The term, stereoselective or stereoselectivity, means without limitation, by way of explanation, the property of a chemical reaction in which a single reactant forms an unequal mixture of stereoisomers during the non-stereospecific creation of a new stereocenter or during the non-stereospecific transformation of a pre-existing one. The selectivity arises from differences in steric effects and electronic effects in the mechanistic pathways leading to the different products.

The literature teaches that the product from the cuprate addition to the aziridine phosphoramidate is regiospecific which has been discovered, is not the case. In fact, the crude product is of acceptable purity to proceed with. Further, it has also been discovered that, where the process generates 3-5% of 6 (a,b,c or d) in the crude product, that it could not be removed later in the synthetic sequence. It was also found that if you used a single solvent (5b crystallizes from heptane or petroleum ether), then you did not remove the corresponding 6b. It is required to leave a residue of the reaction solvent (THF) in the mixture to separate the 5b from 6b. Interestingly, it has been discovered that a ratio of specific solvents yielded the most preferred embodiment. This ratio comprises about 7 part heptane and 1 part THF for 5b, and the other versions of 5 (a, c or d) needed other solvent mixtures, but the common item was that it was required to leave a residue of THF in the mixture.

Experimental Introduction:

Unless otherwise noted, reagents and solvents were used as received from commercial suppliers.

NMR Spectra:

Proton nuclear magnetic resonance spectra were obtained on a Bruker AV 300 or a Bruker AV 500 spectrometer at 300 MHz and 500 MHz, respectively. Spectra are given in ppm (δ) and coupling constants, J, are reported in Hertz. Tetramethylsilane was used as an internal standard for proton spectra.

HPLC Analyses (Achiral):

Analyses were obtained on a Varian Prostar 210 HPLC system using a Prevail C18 column (53×7 mm, Alltech) with PDA detection at 208-210 nm and solvent gradient program Method A.

HPLC Method A:

| Time (min) | Flow (mL/min) | % A | % B |
|---|---|---|---|
| 0.0 | 2.0 | 95.0 | 5.0 |
| 10.0 | 2.0 | 5.0 | 95.0 |
| 11.5 | 2.0 | 5.0 | 95.0 |
| 11.6 | 2.0 | 95.0 | 5.0 |
| 13.0 | 2.0 | 95.0 | 5.0 |

A = Water with 0.05% v/v Trifluoroacetic Acid
B = Acetonitrile with 0.05% v/v Trifluoroacetic Acid HPLC Analyses (Chiral):

Analyses were obtained on a Varian Prostar 210 HPLC system using a CR(−) CrownPak (150×4 mm, 5 um, Diacil Lot #CRM0CB-OK005) with PDA detection at 210-215 nm and isocratic solvent system Method B.

HPLC Method B

Flow rate: 0.7 mL/min

Run time: 35 min

Temp: ambient

Mobile phase: 90% water pH=1.5 (perchloric acid): 10% Methanol

GC (FID):

Analyses were obtained on a Varian CP 3800 GC using a Supleco (Cat #24048) SPB-5 30×0.320; 0.25 μm column.

Column temperature initial: 50° C.

Column temperature final: 275° C.

Ramp profile: 20.0 deg/min

Injector temperature: 250° C.

Detector temperature: 250° C.

Carrier Gas/flow rate: Helium, 2 mL/min

Referring now to the following synthetic schemes, Scheme 1 provides:

Scheme 1

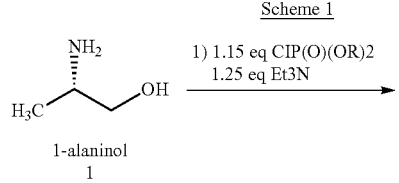

1-alaninol
1

1) 1.15 eq ClP(O)(OR)2
1.25 eq Et3N

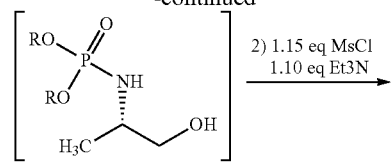

2a-d 2) 1.15 eq MsCl
1.10 eq Et3N

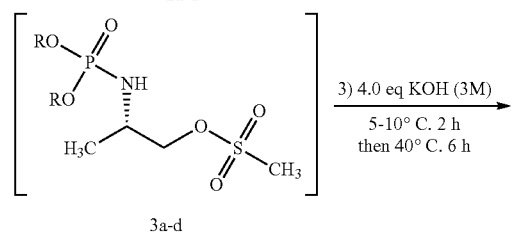

3a-d 3) 4.0 eq KOH (3M)
5-10° C. 2 h
then 40° C. 6 h

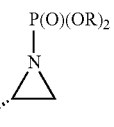

4a-d

| 4 | R | % Yield |
|---|---|---|
| a | Me | 76 |
| b | Et | 81 |
| c | iPr | 42 |
| d | Ph | 30 |

Preparation of
(S)-dimethyl(2-methylaziridin-1-yl)phosphonate (4a)

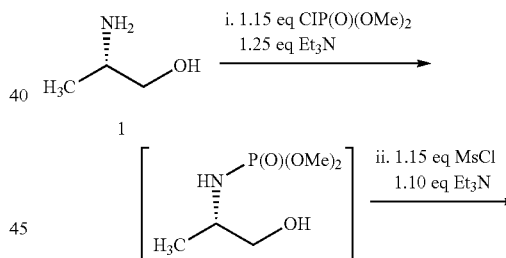

1 i. 1.15 eq ClP(O)(OMe)2
1.25 eq Et3N

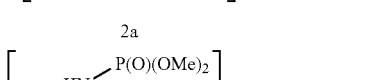

2a ii. 1.15 eq MsCl
1.10 eq Et3N

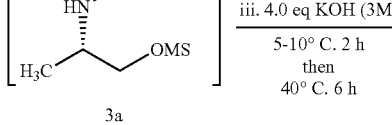

3a iii. 4.0 eq KOH (3M)
5-10° C. 2 h
then
40° C. 6 h

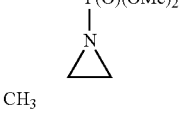

4a

A 500 mL, 3-neck flask equipped with an overhead mechanical stirrer and pressure equalizing addition funnel was charged with L-alaninol (12.5 g, 166.4 mmol), triethylamine (29 mL, 208 mmol, 1.25 equiv) and dichloromethane (125 mL). The reaction solution was cooled to +2° C. and treated with dimethoxyphosphoryl chloride (20 mL, 183 mmol, 1.10 equiv) over 40 minutes while maintaining an internal temperature >+8° C. The reaction mixture was stirred with ice bath cooling for 1 hour at which point the reaction was complete by TLC analysis (silica gel, 93:6:1 DCM/MeOH/NH₄OH and 6/3/1 CHCl₃/MeOH/NH₄OH; KMnO₄ stain). Additional triethylamine (25.5 mL, 182.5 mmol, 1.10 equiv) was added to the reaction mixture and methanesulfonyl chloride (14.9 mL, 191 mol, 1.15 equiv) was added dropwise over 45 minutes while maintaining an internal temperature <+10° C. The resulting reaction mixture was stirred with ice bath cooling for 1.0 hour after which time TLC analysis indicated the reaction was complete. Potassium hydroxide solution (3 M, 220 mL, 650 mmol, 4.0 equiv) was slowly added to the stirred reaction mixture while maintaining an internal temperature <+16° C. The reaction was continued with agitation for 6 hours, after which time the aqueous layer was separated and discarded. Saturated NaHCO₃ solution (35 mL) was added and the biphasic mixture heated to 40-42° C. Distillation was started and a first fraction of 90 mL of dichloromethane was collected. When the temperature reached 50° C., a second fraction was collected until the batch temperature was 65° C. The mixture was heated at 65° C. for another 1 hour and then cooled to ambient temperature. Dichloromethane (90 mL) was added and the mixture stirred for 10 minutes before separation. The dichloromethane layer was concentrated under reduced pressure. The residue was dissolved in heptanes (15 mL) and concentrated under reduced pressure to remove the residual water. This azeotropic drying was repeated two more times. The resulting 4a was obtained as a light yellow liquid (20.9 g, 76% yield, 95.40% GC purity). A colorless sample was prepared by short path distillation (80-85° C.@15 mm Hg vacuum). Optical rotation c=1.00, ethanol, 25.0° C., +39.3°. ¹H NMR (300 MHz, CDCl₃) δ 3.80 (s, 3H), 3.76 (s, 3H), 2.65-2.50 (m, 1H), 2.42-2.31 (m, 1H), 1.92 (dt, J=3.6, 1.2 Hz, 1H), 1.28 (dd, J=5.4, 1.2 Hz, 3H).

Preparation of
(S)-diethyl(2-methylaziridin-1-yl)phosphonate (4b)

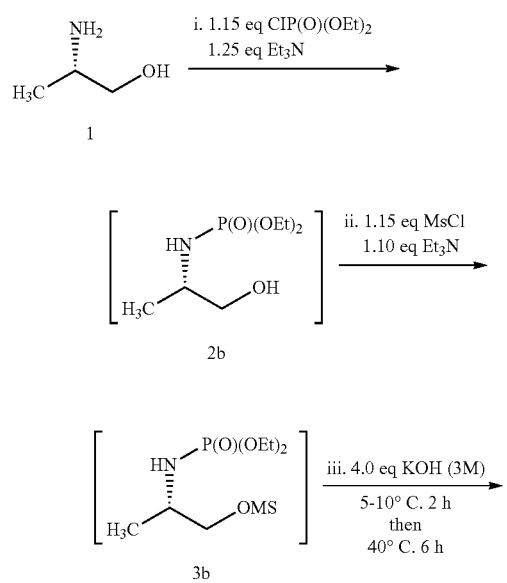

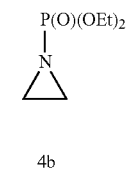

4b

A 12 L 3-neck flask fitted with an overhead mechanical stirrer and 1 L pressure equalizing addition funnel was charged with L-alaninol (250.0 g, 3.33 mol), triethylamine (578 mL, 4.16 mol, 1.25 equiv) and dichloromethane (2.5 L). The stirred solution was cooled to +2° C. and diethoxyphosphoryl chloride (531 mL, 3.661 mol, 1.10 equiv) was added over 1.5 hour while maintaining an internal temperature <+8° C. The reaction mixture was stirred an additional 1 hour at which point the reaction was complete by TLC analysis (silica gel plate, 93:6:1 dichloromethane/MeOH/NH₄OH and 6/3/1 CHCl₃/MeOH/NH₄OH; KMnO₄ stain). Additional triethylamine (510 mL, 3.65 mol, 1.10 equiv) was added to the reaction mixture and methanesulfonyl chloride (297 mL, 3.82 mol, 1.15 equiv) was added drop-wise over 1.5 hours while maintaining an internal temperature <+10° C. The resulting reaction mixture was stirred for 1.5 hours at which time TLC analysis (see above methods) indicated the reaction was complete. Potassium hydroxide solution (3 M solution, 4.40 L, 13 mol, 4.0 equiv) was slowly added to the stirred reaction mixture while maintaining an internal temperature <+16° C. The reaction was stirred for 6 hours, after which time the aqueous layer was separated. Saturated NaHCO₃ solution (700 mL) was added and the biphasic mixture was heated to 40-42° C. Distillation was started and a first fraction of 1.8 L of dichloromethane was collected. When the batch temperature reached 50° C., a second fraction was collected until the batch temperature was 65° C. The mixture was heated at 65° C. for another 1 hour and then cooled to ambient temperature. Dichloromethane (1.8 L) was added and the mixture stirred for 10 minutes before separation. The organic layer was concentrated under reduced pressure and heptane (250 mL) was added to the concentrate. The resulting mixture was concentrated under reduced pressure. The resulting 4b was obtained as a light yellow liquid (518.5 g, 80.6% yield, 98.90% GC purity). A colorless sample was prepared by short path distillation at 66-67° C., 0.9 mm Hg. Optical rotation c=1.01, ethanol, 22.5° C., +28.8°. ¹H NMR (300 MHz, CDCl₃) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Preparation of
(S)-diisopropyl(2-methylaziridin-1-yl)phosphonate
(4c)

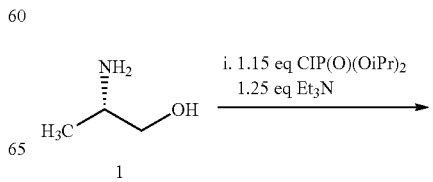

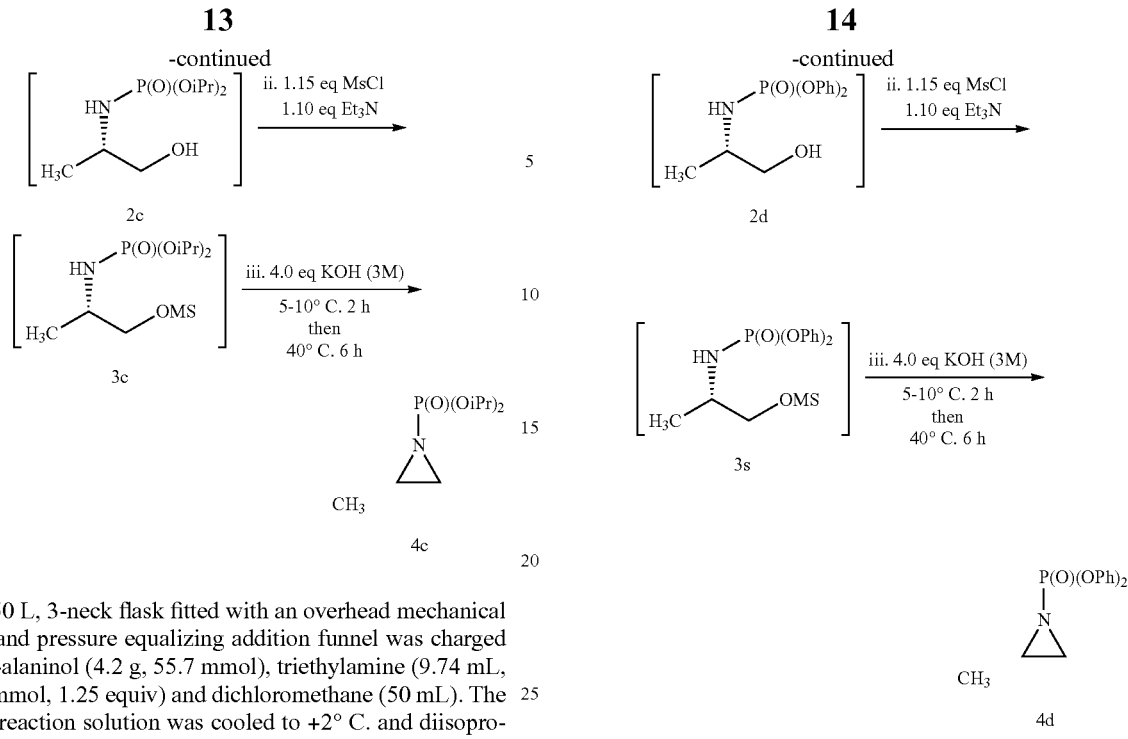

A 250 L, 3-neck flask fitted with an overhead mechanical stirrer and pressure equalizing addition funnel was charged with L-alaninol (4.2 g, 55.7 mmol), triethylamine (9.74 mL, 69.68 mmol, 1.25 equiv) and dichloromethane (50 mL). The stirred reaction solution was cooled to +2° C. and diisopropylphosphoryl chloride (12.3 g, 61.3 mmol, 1.10 equiv) was added drop-wise over 1.3 hours maintaining an internal temperature <+8° C. The reaction mixture was stirred at about 0° C. for 10 hours. At this point, the reaction was complete by TLC analysis (silica gel, 93:6:1 DCM/MeOH/NH$_4$OH and 6/3/1 CHCl$_3$/MeOH/NH$_4$OH; KMnO$_4$ stain). Additional triethylamine (8.6 mL, 61.3 mmol, 1.10 equiv) was added to the reaction mixture and methanesulfonyl chloride (4.96 mL, 64.1 mmol, 1.15 equiv) was added over 1.5 hours maintaining an internal temperature <+10° C. The resulting reaction mixture was stirred at about 0° C. for 1.5 hours after which time TLC analysis (see above) indicated the complete consumption of 2c and formation of 3c. Potassium hydroxide solution (3 M solution, 74 mL, 222.9 mmol, 4.0 equiv) was slowly added to the stirred reaction mixture while maintaining an internal temperature <+16° C. The reaction was continued with agitation for 6 hours, after which time the layers were separated. The organic layer was washed with 10% citric acid solution (40 mL) and saturated NaCl solution (2×40 mL). The organic layer was concentrated under reduced pressure and the residue was distilled (bulb-to-bulb; 79-82° C. @3 mm Hg vacuum) to afford 4c as a clear colorless liquid (5.2 g, 42.0% yield, 97.0% GC AUC purity). Optical rotation c=1.01, ethanol, 22.5° C., +28.8°. $^1$H NMR (300 MHz, CDCl$_3$) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H), 1.22 (dd, J=5.6, 1.2 Hz, 3H).

Preparation of (S)-diphenyl(2-methylaziridin-1-yl)phosphonate (4d)

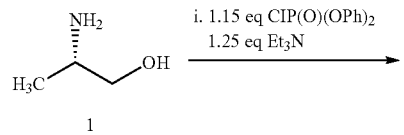

A 500 L 3-neck flask fitted with an overhead mechanical stirrer and a pressure equalizing addition funnel was charged L-alaninol (8.5 g, 113 mmol), triethylamine (19.5 mL, 139.36 mmol, 1.25 equiv) and dichloromethane (100 mL). The stirred reaction mixture was cooled to +2° C. and treated with diphenylchlorophosphate (33.4 g, 124.3 mmol, 1.10 equiv) over 1 hour while maintaining an internal temperature <+8° C. The reaction mixture was stirred for 10 hours at which point the reaction was complete by TLC analysis (silica gel, 93:6:1 DCM/MeOH/NH$_4$OH and 6/3/1 CHCl$_3$/MeOH/NH$_4$OH; KMnO$_4$ stain). Additional triethylamine (17.5 mL, 123 mmol, 1.10 equiv) was added to the reaction mixture and methanesulfonyl chloride (10 mL, 129.1 mmol, 1.15 equiv) was added over 50 minutes while maintaining an internal temperature <+10° C. The resulting reaction mixture was stirred with ice bath cooling for 1.5 hours after which time TLC analysis (see above) indicated the reaction was complete. Potassium carbonate (61.5 g, 445 mmol, 4.0 equiv) was added to the cooled, stirred reaction mixture while maintaining an internal temperature <+16° C. The reaction mixture was stirred for 6 hours at ambient temperature. The solid was filtered and the organic phase was washed with 10% citric acid solution (40 mL) and saturated NaCl solution (2×40 mL). The organic solution was concentrated under reduced pressure and the residue was purified by column chromatography. The resulting 4d was obtained as viscous oil (9.8 g, 30.0% yield, 97.0% GC purity). Optical rotation c=1.00, ethanol, 25.1° C., +34.8°. $^1$H NMR (300 MHz, CDCl$_3$) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H), 1.22 (dd, J=5.6, 1.2 Hz, 3H).

Referring now to the following synthetic scheme, Scheme 2 provides:

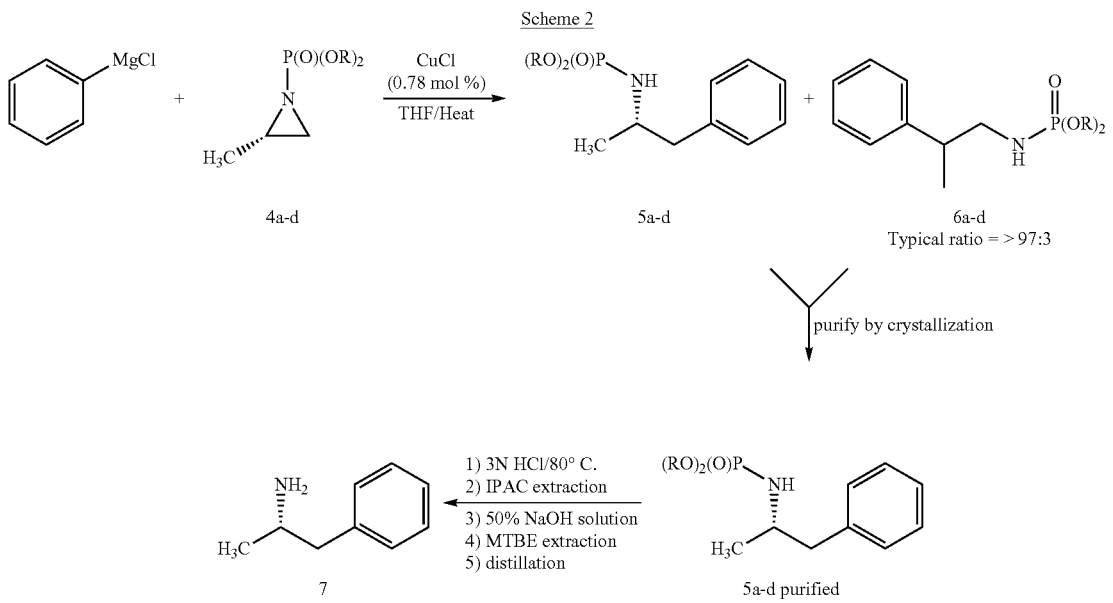

The phosphoryl chlorides were either purchased or prepared as per Posheus, Herweh, J. Am. Chem. Soc. 1957, 79, 6127-6129.

Preparation of
(S)-dimethyl(1-phenylpropan-2-yl)phosphoramidate
(5a)

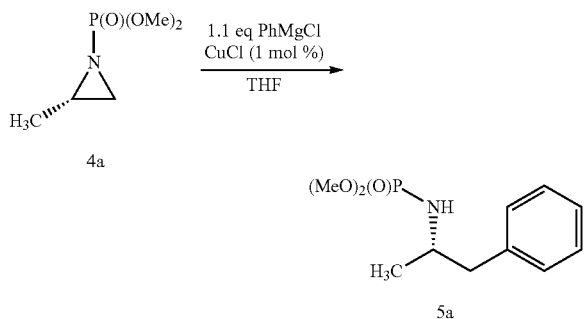

A 100 mL 3-neck flask was charged with 4a (4.0 g, 24.2 mmol), THF (25 mL) and CuCl (28 mg, 1 mol %) and the stirrer was started. The mixture was heated to 48° C. A pressure equalizing addition funnel was charged with PhMgCl (2M in THF, 13 mL) and the solution was added slowly while maintaining an internal temperature between 48-51° C. The reaction was stirred at 48-51° C. for an additional 30 minutes and then cooled to ambient temperature. The reaction was quenched by slow addition to a cooled (15° C.) solution of saturated aqueous ammonium chloride in water (50/50 v/v, 40 mL) while maintaining the temperature below 20° C. Heptanes (40 mL) was used to rinse the reactor and the rinse solution was transferred to the quenched reaction mixture. The mixture was agitated for 5 minutes, allowed to separate for 20 minutes then the aqueous phase was discarded. The organic phase washed with deionized water (10 mL) and the organic phase concentrated under reduced pressure to give an oil. The residue was dissolved in heptanes (50 mL) and the solution was concentrated under reduced pressure. The residue was crystallized from methyl tert-butyl ether (1 g/3 mL), filtered and dried to give 5a as white needles (3.29 g; 60.2% yield), with 99.89% GC purity containing 0.05% 6a. mp 86-88° C. Optical rotation c=1.00, ethanol, 25.0° C., +29.7°. $^1$H NMR (300 MHz, CDCl$_3$) δ 7.32-7.17 (m, 5H), 3.66 (d, J=6.4 Hz, 3H), 3.50-3.83 (m, 1H), 2.71 (d, J=6.6 Hz, 2H), 2.45 (m, 1H), 1.15 (d, J=6.6 Hz, 3H).

Preparation of Dexamphetamine (7) from 5a

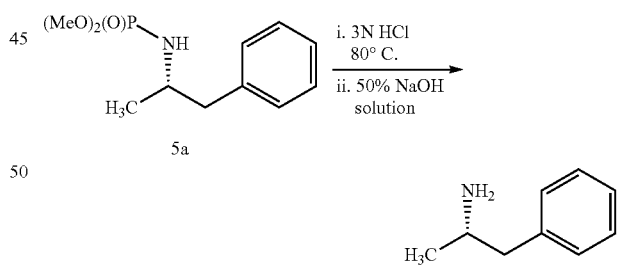

A 50 mL flask was charged with 5a (4.80 g, 19.73 mmol) and 3 M HCl (15.0 mL) and the stirred reaction mixture was heated to 80° C. for 1 hour, then cooled to room temperature. The reaction mixture was washed with isopropyl acetate (2×20 mL) and the organic extracts were disposed. The aqueous layer was treated with sodium hydroxide solution (50%, 12.0 mL) keeping the internal temperature below 25° C. Methyl tert-butyl ether (15 mL) was added and the reaction mixture was agitated for 5 minutes then allowed to separate. The organic layer washed with water (10 mL) and concentrated under reduced pressure to give 7 as a colorless oil (2.51 g, 94.4% yield, >99.5% purity by GC and chiral HPLC).

Preparation of (S)-diethyl(1-phenylpropan-2-yl) phosphor-amidate (5b)

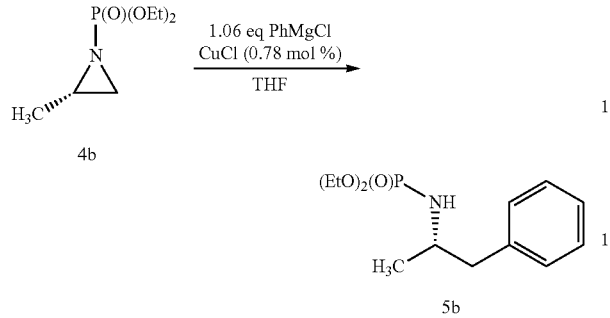

A 12 L, jacketed, bottom outlet flask was charged with 4b (500 g, 2.58 mol), THF (2.5 L) and CuCl (2.0 g, 0.78 mol %) and the stirred mixture was heated to 46° C. A pressure equalizing addition funnel was charged with PhMgCl (2M in THF, 1.6 L) and the solution was added slowly while maintaining an internal temperature between 48-51° C. After the addition was complete, the reaction mixture was stirred at 48-51° C. for an additional 30 minutes and then cooled to ambient temperature. The reaction was quenched by slow addition to a cooled mixture of saturated aqueous ammonium chloride solution and water (50/50 v/v, 3.0 L) while maintaining an internal temperature below 20° C. The flask was rinsed with heptanes (2.0 L) and the rinse was transferred to the quenched reaction mixture. The biphasic mixture was stirred for 5 minutes, allowed to separate for 20 minutes and then the aqueous phase was removed. The organic phase washed with deionized water (500 mL) and the organic phase concentrated under vacuum to a volume of about 1.0 L. Heptanes (1000 mL) was added and the solution volume was adjusted by reduced pressure distillation to a total volume of about 1.5 L. The stirrer was slowed and the crystallization was allowed to proceed for about 24 hours. The slurry was cooled to 5° C. for about 1.5 hours. The resulting crystalline solid was collected by vacuum filtration and washed with cold heptanes (2×200 mL). After drying under vacuum at 35° C. for 48 hours the (S)-diethyl(1-phenylpropan-2-yl)phosphoramidate (5b) was obtained as a white crystalline solid (565.0 g, 80.5% yield; 99.66% GC purity with 0.04% 6b present), mp 64-65° C. Optical rotation c=1.10, ethanol, 22.5° C., +27.7°. $^1$H NMR (300 MHz, CDCl$_3$) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

Alternate Preparation of (S)-diethyl(1-phenylpropan-2-yl)phosphoramidate (5b) using Cu nanoparticles A 250 mL 3-necked flask was charged with 4b (10 g, 51.8 mmol), THF (50 mL) and copper nanopowder (65 mg, 2 mol %) and the stirred mixture was heated to 50° C. A pressure equalizing addition funnel was charged with PhMgCl (2M in THF, 29 mL) and the reagent was added while maintaining an internal temperature of 50-52° C. The reaction was allowed to stir at 50-52° C. for an additional 16 hours and then cooled to ambient temperature. The reaction was quenched by slow addition to a cooled (15° C.) solution of saturated aqueous ammonium chloride/water (50/50 v/v, 50 L) while maintaining an internal temperature below 20° C. Heptanes (50 L) was used to rinse the reactor and this rinse was transferred to the quenched mixture. The mixture was agitated for 5 minutes, allowed to separate and the aqueous phase was removed. The organic phase washed with deionized water (50 mL) and the organic phase concentrated under reduced pressure to a volume of about 15 mL. Heptanes (50 mL) were added and the solution was evaporated under reduced pressure volume to a total volume of about 15 mL. The solution was slowly stirred for about 24 hours affording a white slurry which was cooled to 5° C. for about 1.5 hours. The resulting crystalline solid was collected by filtration and washed with cold heptanes (2×10 mL). After drying under reduced pressure at 35° C. for 48 hours, 5b was obtained as a white crystalline solid (8.6 g, 60.5% yield, 99.90% GC purity).

Alternate Preparation of (S)-diethyl(1-phenylpropan-2-yl)phosphoramidate (5b) Using Cu(II) Chloride A 250 mL 3-neck flask was charged with 4b (10 g, 51.8 mol), THF (50 mL) and CuCl$_2$ (70 mg, 1 mol %) after which time the mixture was heated to about 50° C. A pressure equalizing addition funnel was charged with PhMgCl (2M in THF, 29 mL) and the reagent was added slowly while maintaining an internal temperature between 50-52° C. The reaction was allowed to stir at 50-52° C. for an additional 16 hours and then cooled to ambient temperature. The reaction was quenched by slow addition to a cooled (about 15° C.) solution of saturated aqueous ammonium chloride/water (50/50 v/v, 50 mL) while maintaining an internal temperature below 20° C. Heptanes (50 mL) was used to rinse the reactor and was transferred to the quench mixture, the mixture was agitated for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution was concentrated under reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 48 h, 5b was obtained as a white crystalline solid (8.7 g, 60.0% yield, 99.90% GC purity).

Alternate Preparation of (S)-diethyl(1-phenylpropan-2-yl)phosphoramidate (5b) using CuBr

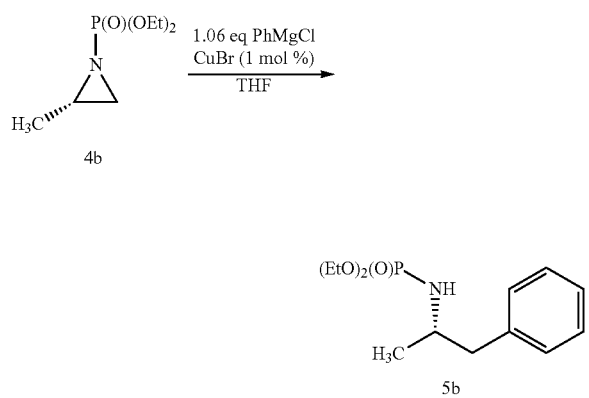

A 250 mL 3-neck flask was charged with 4 (10 g, 51.8 mol), THF (50 mL) and CuBr (74.4 mg, 1 mol %) after which time the mixture was heated to about 50° C. A pressure equalizing addition funnel was charged with PhMgCl (2M in THF, 29 mL) and the reagent was added slowly while maintaining an internal temperature between 48-52° C. The reaction was allowed to stir at 50-52° C. for an additional 16 hours and then cooled to ambient temperature. The reaction was quenched by slow addition to a cooled (about 15° C.) solution of saturated aqueous ammonium chloride/water (50/50 v/v, 50 mL) while maintaining an internal temperature below 20° C. Heptanes (50 mL) was used to rinse the reactor and was transferred to the quench mixture. The mixture was stirred for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution was adjusted by reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 48 h, 5b was obtained as a white crystalline solid (9.1 g, 65% yield, 99.90% GC purity).

The use of other copper salts (CuF, Cu(OAc)$_2$, Cu(acac)$_2$, Cu(OMe)$_2$ and Copper turnings) in conversion to 4b to 5b, conducted under the established procedure afforded 5b in comparable isolated yield, GC purity and devoid of the regioisomer 6b.

Alternate Preparation of (S)-diethyl(1-phenylpropan-2-yl)phosphoramidate (5b) in THF-toluene Mixture

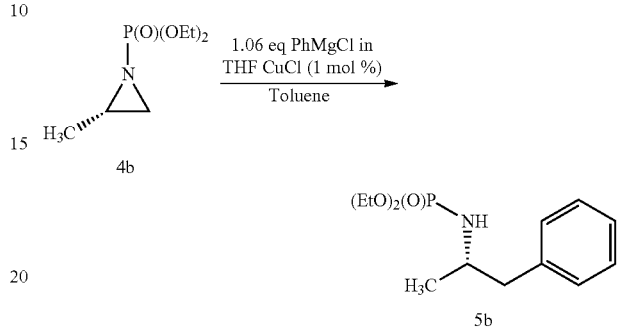

A 250 mL 3-neck flask was charged with 4b (10 g, 51.8 mol), toluene (50 mL) and CuCl (51 mg, 1 mol %) after which time the mixture was heated to about 50° C. A dropping addition funnel was charged with PhMgCl (2M in THF, 29 mL) and the reagent was added slowly while maintaining an internal temperature between 48-52° C. The reaction was allowed to stir at 50-52° C. for an additional 16 hours and then cooled to ambient temperature. The reaction was quenched by slow addition to a cooled (15° C.) solution of saturated aqueous ammonium chloride/water (50/50 v/v, 50 mL) while maintaining an internal temperature below 20° C. Heptanes (50 mL) was used to rinse the reactor and was transferred to the quench mixture, the mixture was agitated for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution volume was adjusted by reduced pressure to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 36 hours, 5b was obtained as a white crystalline solid (8.7 g, 62% yield, 99.92% GC purity).

Alternate Preparation of (S)-diethyl(1-phenylpropan-2-yl)phosphoramidate (5b) in THF-methyl tert-butyl Ether Mixture

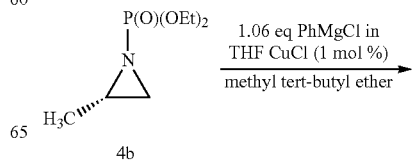

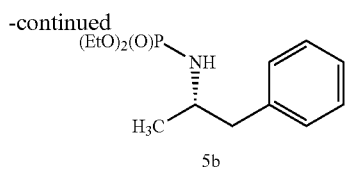

A 250 mL 3-neck flask was charged with 4 (10 g, 51.8 mol), methyl tert-butyl ether (50 mL) and CuCl (51 mg, 1 mol %) after which time the mixture was heated to about 50° C. A pressure equalizing addition funnel was charged with PhMgCl (2M in THF, 29 mL) and the reagent was added slowly while maintaining an internal temperature between 48-52° C. The reaction was allowed to stir at 50-52° C. for an additional 16 hours and then cooled to ambient temperature. The reaction was quenched by slow addition to a cooled (15° C.) solution of saturated aqueous ammonium chloride/water (50/50 v/v, 50 mL) while maintaining an internal temperature below 20° C. Heptanes (50 mL) was used to rinse the reactor and was transferred to the quench mixture. The mixture was agitated for 5 minutes, allowed to separate for 20 minutes and then the aqueous phase was removed. The organic phase washed with deionized water (50 mL) and the organic phase concentrated under reduced pressure to a volume of about 15 mL. Heptanes (50 mL) was added and the solution volume was adjusted by reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 24 hours, 5b was obtained as a white crystalline solid (8.8 g, 63% yield, 99.93% GC purity).

Alternate Preparation of (S)-diethyl(1-phenylpropan-2-yl)phosphoramidate (5b) in THF-2 methyl THF Mixture

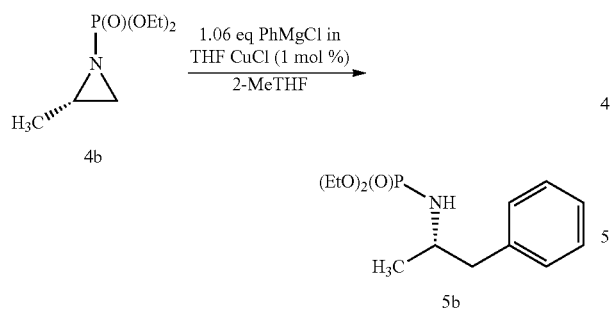

A 250 mL 3-neck flask was charged with 4 (10 g, 51.8 mol), 2-MeTHF (50 mL) and CuCl (51 mg, 1 mol %) after which time the mixture was heated to about 50° C. A pressure equalizing addition funnel was charged with PhMgCl (2M in THF, 29 mL) and the reagent was added slowly while maintaining an internal temperature between 48-52° C. The reaction was allowed to stir at 50-52° C. for an additional 12 hours and then cooled to ambient temperature. The reaction was quenched by slow addition to a cooled (15° C.) solution of saturated aqueous ammonium chloride/water (50/50 v/v, 50 mL) while maintaining an internal temperature below 20° C. Heptanes (50 mL) was used to rinse the reactor and was transferred to the quench mixture. The mixture was agitated for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution volume was adjusted by reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 24 hours, 5b was obtained as a white crystalline solid (9.1 g, 65% yield, 99.89% GC purity).

Preparation of Dexamphetamine (7) from 5b

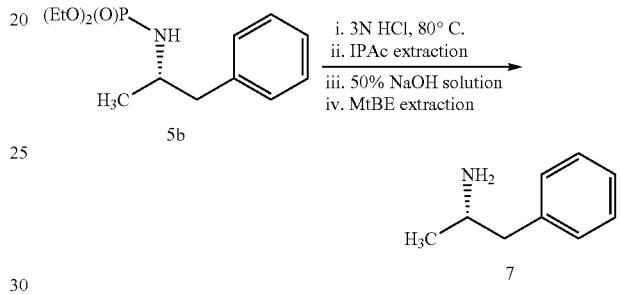

A 2 L, jacketed, bottom outlet valve flask was charged with 5b (209 g, 0.770 mol) and 3 M hydrochloric acid (510 mL) and the reaction mixture was heated to 80° C. for 1.5 hours and then cooled to room temperature. The orange solution was extracted with isopropyl acetate (500 mL) and the organic extract layer was discarded. Sodium hydroxide solution (50%, 175 mL) was slowly added to the remaining aqueous layer, keeping the internal temperature below 25° C. Methyl tert-butyl ether (200 mL) was added and the reaction mixture was agitated for 20 minutes then allowed to separate for 30 minutes. The aqueous layer was removed and the organic layer washed with water (100 mL) and concentrated under reduced pressure to afford a light brown oil. This oil was distilled (Distillation conditions: 1" wipe film still, T=65-90° C., vacuum=4-5 mmHg, wiper speed=490-520 rpm.) to give dexamphetamine (7) as a clear colorless oil (81 g, 78% yield; >99.8% pure by GC). Chiral HPLC analysis: 99.83% dextroampehtamine; 0.16% levoamphetamine; 99.67% ee. Optical rotation c=2.0, methanol, 22.0° C., +29.2°. $^1$H NMR (300 MHz, CDCl$_3$) δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H).

Preparation of (5)-diisopropyl(1-phenylpropan-2-yl)phosphoramidate (5c)

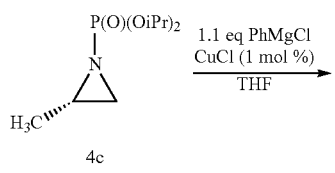

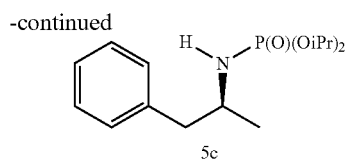

A 100 mL jacketed flask equipped with an overhead stirrer was charged with 4c (5.0 g, 22.6 mmol), THF (25 mL) and CuCl (23 mg, 1 mol %). The stirrer was started and the mixture was heated to 48° C. A pressure equalizing addition funnel was charged with PhMgCl (2M in THF, 12.4 mL) and this solution was added while maintaining the internal temperature of 48-51° C. The reaction was allowed to stir at 48-51° C. for 30 minutes after Grignard addition and then cooled to 20° C. The reaction was quenched by slow addition to a pre-cooled (15° C.) solution of saturated aqueous ammonium chloride solution in water (50/50 v/v, 40 mL) while maintaining an internal temperature below 20° C. Heptanes (40 mL) was used to rinse the reactor and the rinse solution was added to the quench mixture. The mixture was agitated for 5 minutes, allowed to separate for 20 minutes and then the aqueous phase was removed. The organic phase washed with deionized water (10 mL) and the organic phase concentrated under reduced pressure. The residue was dissolved in heptanes (50 mL) and the solution was concentrated to dryness under reduced pressure. The residue was purified by chromatography (120 g Combiflash Gold column eluting with 100% dichloromethane to 5% MeOH in dichloromethane over a 40 minute gradient). The appropriate fractions were concentrated to dryness under reduced pressure to give the desired product as a slow crystallizing solid (4.4 g, 65%, 92% GC purity). The GC analysis indicated the presence of 5% biphenyl as well as ~0.8% of 6c. A 1 g sample was removed and crystallized from 1 volume cold heptanes at −15° C. The resulting crystals of 5c (0.421 mg, 42% recovery) were found to be 99.75% pure by GC analysis with 0.09% of 6c. The crystalline 5c melted when the sample reached room temperature. Optical rotation c=1.10, ethanol, 22.5° C., +27.7°. $^1$H NMR (300 MHz, CDCl$_3$) δ 7.32-7.17 (m, 5H), 4.59-4.41 (m, 2H), 3.53-3.41 (m, 1H), 2.86-2.80 (m, 1H), 2.69-2.61 (m, 1H), 2.36 (t, J=9.6 Hz, 1H), 1.32-1.26 (m, 12H), 1.08 (d, J=10.1 Hz, 3H).

Preparation of Dexamphetamine (7) from 5c

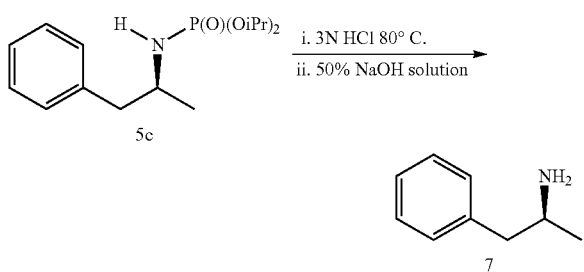

A 50 mL flask was charged with 5c (3.54 g, 11.82 mmol) and 3 M HCl (8.7 mL) and the stirred reaction mixture was heated to 80° C. for 12 hours, then cooled to room temperature. The aqueous solution was washed with isopropyl acetate (2×20 mL) and the organic extract was discarded. The aqueous layer was treated with sodium hydroxide solution (50%, 3.0 mL) keeping the internal temperature below 25° C. Methyl tert-butyl ether (40 mL) was added and the reaction mixture was agitated for 5 minutes then allowed to separate for 15 minutes. The aqueous layer was extracted with methyl tert-butyl ether (40 mL) and the combined organic layers were washed with water (10 mL) and concentrated under reduced pressure to give 7 as a colorless oil (1.28 g, 80.3% yield, >98.7% purity by GC and chiral HPLC).

Preparation of (S)-diphenyl(1-phenylpropan-2-yl)phosphoramidate (5d)

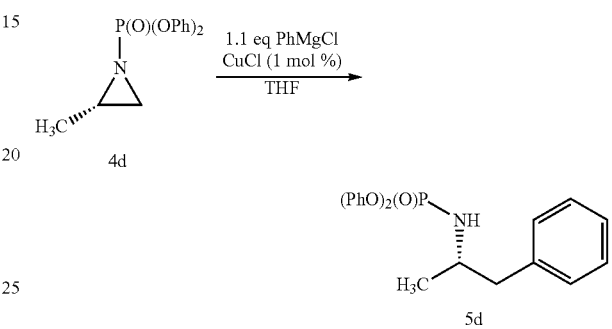

A 100 mL jacketed flask was charged with 4d (5.0 g, 17.3 mmol), THF (25 mL) and CuCl (21 mg, 1 mol %) and the stirred mixture was heated to 48° C. A pressure equalizing addition funnel was charged with PhMgCl (2M in THF, 8.7 mL) and the solution was added slowly while maintaining a reaction temperature of 48-51° C. The reaction was allowed to stir at 48-51° C. for an additional 30 minutes and then cooled to ambient temperature. The reaction was quenched by slow addition to a cooled (15° C.) solution of saturated aqueous ammonium chloride/water mixture (50/50 v/v, 30 mL) while maintaining the batch temperature below 20° C. Heptanes (30 mL) was used to rinse the reactor and was transferred to the quench mixture. The mixture was agitated for 5 minutes and the aqueous layer was removed. The organic layer washed with deionized water (8 mL) and the organic phase concentrated under reduced pressure to give an oil. This residue was dissolved in heptanes (30 mL) and the solution was concentrated under reduced pressure to afford a residue. The residue was crystallized from ethanol (1 g/5 mL) to give 5d as a white solid (3.14 g, 50% yield, 99.65% GC purity containing 0.05% of 6d), mp 102-103° C. (lit 101-102° C.). Optical rotation c=1.00, ethanol, 25.0° C., +18.4°. $^1$H NMR (300 MHz, CDCl$_3$) δ 7.38-7.11 (m, 15H), 3.83-3.65 (m, 1H), 3.00-2.89 (m, 1H), 2.86-2.78 (m, 1H), 2.73-2.62 (m, 1H), 1.15 (d, J=10.1 Hz, 3H).

Preparation of Dexamphetamine (7) from 5d

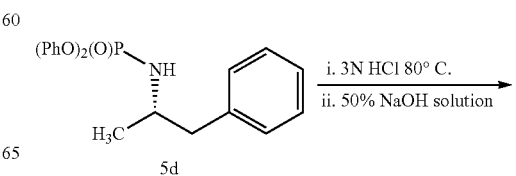

-continued

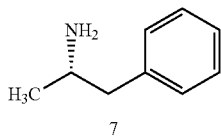

7

A 50 mL flask was charged with 5d (7.24 g, 19.71 mmol) and 3 M HCl (15.0 mL) and the stirred reaction mixture was heated to 80° C. for 32 hours, at which point it was cooled to room temperature. The organic layer was washed with isopropyl acetate (2×20 mL) and the organic extracts were discarded. The aqueous layer was treated with sodium hydroxide solution (50%, 3.0 mL) keeping the internal temperature below 25° C. Methyl tert-butyl ether (40 mL) was added and the reaction mixture was agitated for 5 minutes and then separated. A second portion of methyl tert-butyl ether (40 mL) was added and the reaction mixture was agitated for 5 minutes. The combined organic extracts were washed with water (10 mL) and concentrated under reduced pressure to give 7 as a colorless oil (2.05 g, 76.9% yield, >99% GC purity).

Preparation of Impurities 6a-d

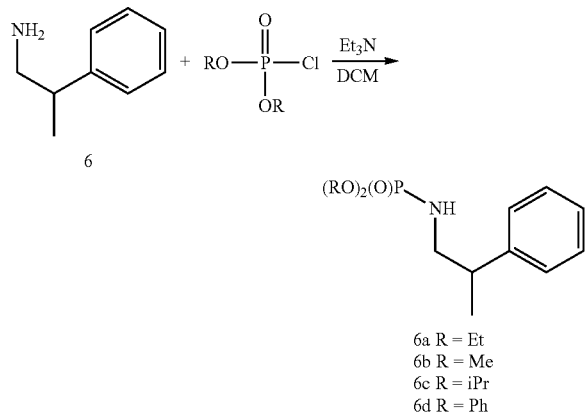

6a R = Et
6b R = Me
6c R = iPr
6d R = Ph

A 100 mL 3-neck flask was charged with 6 (1.0 g, 7.4 mmol), Et₃N (1.23 mL, 8.8 mmol), and dichloromethane (25 mL). The solution was cooled to 0-5° C. and a solution of chlorophosphate (8.15 mmol) in dichloromethane (5 mL) was added over 5 minutes. The reaction mixture was allowed to stir at ambient temperature overnight. The reaction mixture was then quenched by adding water (20 mL) and the organic layer was separated. The organic extract was washed with 1N HCl solution (10 mL), saturated NaHCO₃ solution (10 mL), and saturated sodium chloride solution (10 mL). The organic phase was concentrated to dryness to afford the desired product, 6a-d.

6a: 81% yield, colorless oil. 95.8% GC purity. $^1$H NMR (300 MHz, CDCl₃) δ7.30-7.19 (m, 5H), 3.68 (d, J=11.1 Hz, 3H), 3.63 (d, J=11.1 Hz, 3H), 3.20-3.00 (m, 2H), 2.95-2.80 (m, 1H), 2.45 (s, br, 1H), 1.26 (d, J=6.9 Hz, 3H).

6b: 85% yield, colorless oil. 97.47% GC purity $^1$H NMR (300 MHz, CDCl₃) δ 7.32-7.19 (m, 5H), 4.04-3.91 (m, 4H), 3.20-3.95 (m, 2H), 2.92-2.80 (m, 1H), 2.45 (s, br, 1H), 1.26 (d, J=6.9 Hz, 3H).

6c: The residue was chromatographed on a 40 g Combiflash Gold column eluting with 100% heptanes to 100% ethyl acetate over a 20 minute gradient. Combined clean fractions we concentrated to dryness to give the desired product as a clear colorless oil in 42% yield, 97.3% purity GC. $^1$H NMR (300 MHz, CDCl₃) δ 7.37-7.10 (m, 5H), 4.61-4.44 (m, 2H), 3.20-2.91 (m, 2H), 2.90-2.78 (m, 1H), 2.41-2.28 (m, 1H), 1.35-1.16 (m, 15H).

6d: 91% yield, colorless oil. 95.16% GC purity. $^1$H NMR (300 MHz, CDCl₃) δ 7.26-7.04 (m, 15H), 3.48 (s, br, 1H), 3.35-3.22 (m, 1H), 3.03-2.90 (m, 2H), 1.21 (m, 3H).

Referring now to the following Scheme, Scheme 3 provides synthetic routes to the ethyl and methyl derivatives.

Scheme 3

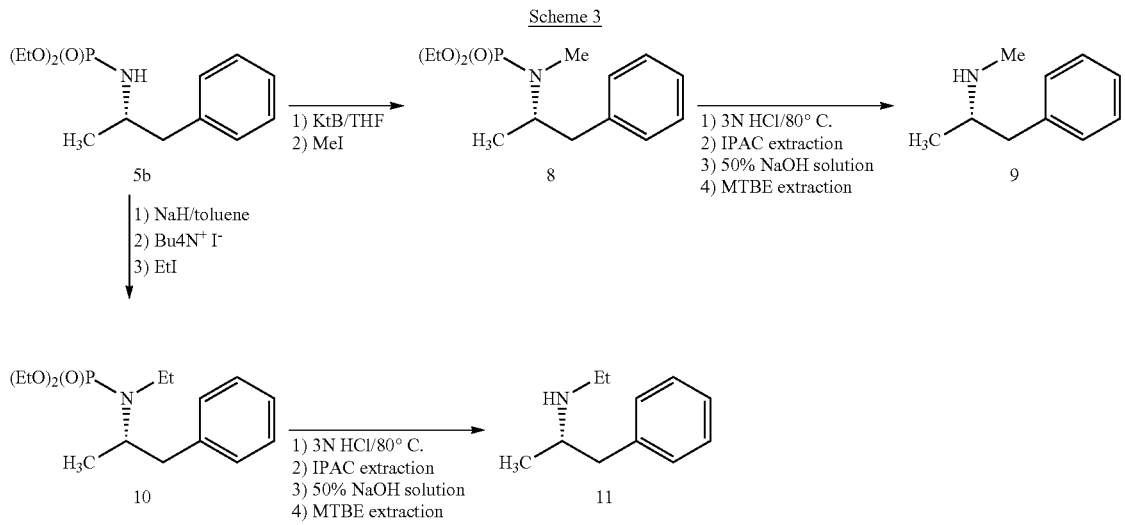

Note: both compounds isolated as their respective HCl salts mp and optical rotation matched the literature values

Preparation of (S)-diethyl methyl(1-phenylpropan-2-yl)phosphoramidate (8) from 5b

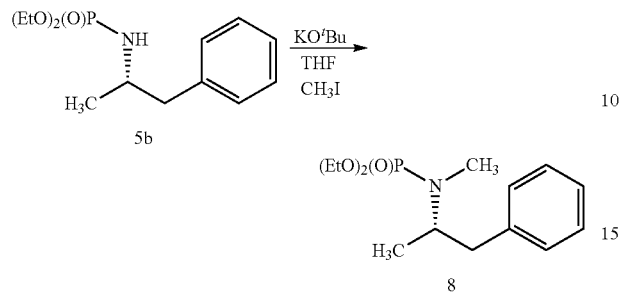

A 100 mL, 3 neck flask was charged with 5b (1.00 g, 3.68 mmol) and dry THF (40 mL). Stirring was started and once a solution was obtained, potassium tert-butoxide (0.455 g, 4.05 mmol, 1.1 eq) was added. The mixture was stirred at room temperature for 10 minutes followed by the addition of iodomethane (0.252 mL, 4.05 mmol, 1.1 eq). The reaction was followed by TLC analysis (silica gel plates; 1:1 hexanes/ethyl acetate and 95:5 dichloromethane/methanol) and additional base and iodomethane was added until the reaction was complete. The reaction was quenched with NaCl solution (20 mL) and extracted with ethyl acetate (40 mL). The organic extract was dried with anhydrous sodium sulfate, filtered and concentrated under reduced pressure. The residue was chromatographed (40 g Combiflash column, 100% heptane to 100% ethyl acetate eluent) and appropriate fractions were combined and evaporated to afford 8 as a colorless oil (0.511 g, 48% yield). Optical rotation c=1.10, ethanol, 25.2° C., +36.5°. $^1$H NMR (300 MHz, CDCl$_3$) δ 7.32-7.18 (m, 5H), 4.10-3.85 (m, 2H), 3.81-3.79 (m, 2H), 3.62-3.44 (m, 1H), 2.87-2.73 (m, 1H), 2.72-2.90 (m, 1H), 2.55 (d, J=9.6 Hz, 3H), 1.24 (t, J=6.8 Hz, 3H), 1.18-1.05 (m, 6H).

Preparation of d-N-methylamphetamine (9) from 8

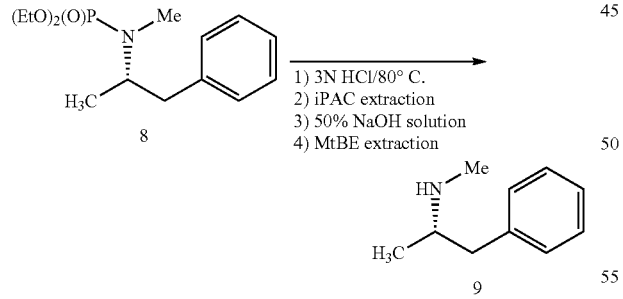

A 50 mL, 3-necked round bottomed flask was charged with 8 (0.5 g, 1.75 mmol) and 3 M HCl (25 mL) and the stirred reaction mixture was heated to 80° C. for 2.5 hours and then cooled to room temperature. The orange solution was extracted with isopropyl acetate (25 mL) and the organic extract layer was discarded. Sodium hydroxide solution (50% solution, 10 mL) was slowly added to the remaining aqueous layer, keeping the internal temperature below 25° C. Methyl tert-butyl ether (20 mL) was added and the reaction mixture was agitated for 20 minutes then allowed to separate for 30 minutes. The aqueous layer was removed and the organic layer washed with water (10 mL), dried over anhydrous sodium sulfate, filtered and concentrated under reduced pressure to give a light brown oil. This oil was distilled (bulb-to-bulb at 65-67° C. @0.6 mm Hg vacuum) to afford 9 as a colorless oil (0.19 g, 75% yield). This distillate was converted to the known HCl salt for analysis, mp 172-175° C. Optical rotation c=1.00, water, 25.2° C., +16.3°.

Preparation of (S)-diethyl ethyl(1-phenylpropan-2-yl)phosphoramidate (10) from 5b

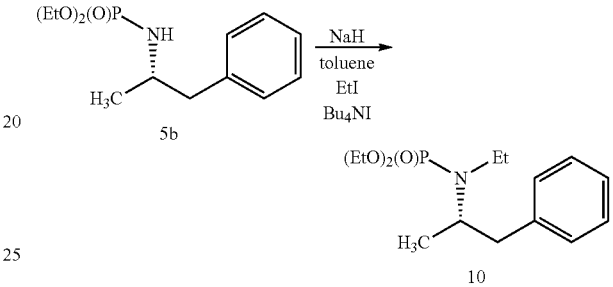

A 100 mL, 3-neck flask was charged with toluene (40 mL) and 5b (5.58 g, 20 mmol) and the mixture was stirred until a solution was obtained. To this solution was added sodium hydride (60% suspension in mineral oil, 0.880 g, 22.0 mmol, 1.1 eq) followed by tetrabutylammonium iodide (0.369 g, 1 mmol,) and iodoethane (2.41 mL, 30 mmol). The mixture was heated to 80° C. for 4 hours. Additional portions of iodoethane (0.200 mL) and sodium hydride (0.100 g) were added which resulted in complete consumption of 5b. The reaction was cooled to room temperature, quenched with NaCl solution (20 mL). The layers were separated and the aqueous phase extracted with toluene (40 mL). The combined organic phases were dried with anhydrous sodium sulfate, filtered and concentrated to a brown oily residue. This residue was chromatographed (40 g Combiflash column, 100% heptane to 100% ethyl acetate eluent) and product fractions were combined and evaporated under reduced pressure to give 10 as a clear, pale yellow oil (3.78 g, 12.6 mmol, 63% yield). Optical rotation c=1.00, ethanol, 25.0° C., +35.6°. $^1$H NMR (300 MHz, CDCl$_3$) δ 7.31-7.10 (m, 5H), 4.08-3.62 (m, 5H), 3.11-2.88 (m, 3H), 2.76-2.67 (m, 1H), 1.32-1.21 (m, 6H), 1.20-1.10 (m, 6H).

Preparation of d-N-ethylamphetamine (11) from 10

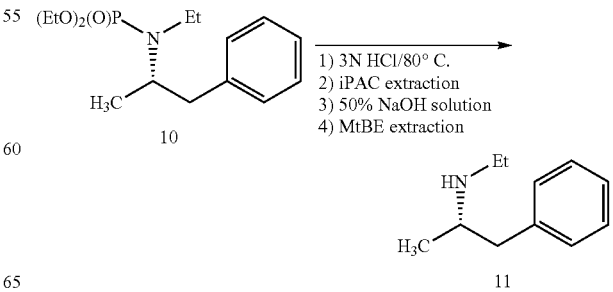

A 50 mL round bottomed flask was charged with 10 (2.5 g, 8.3 mmol) and 3 M HCl (25 mL) and the stirred reaction mixture was heated to 80° C. for 3.25 hours and cooled to room temperature. The orange solution was extracted with isopropyl acetate (25 mL) and the organic extract layer was discarded. Sodium hydroxide solution (50% solution, 25 mL) was slowly added to the remaining aqueous layer, keeping the internal temperature below 25° C. Methyl tert-butyl ether (20 mL) was added and the reaction mixture was agitated for 20 minutes and allowed to separate for 30 minutes. The aqueous layer was removed and the organic layer washed with water (10 mL) and concentrated under reduced pressure to give a brown oily residue. This residue was distilled (bulb-to-bulb; 105-106° C. @14.0 mm Hg vacuum) to give 11 as a colorless oil (1.10 g, 81% yield).

Distillation: 105-106° C., 14.0 mm Hg. This oil was converted to the known HCl salt for analysis, mp 154-156° C. Optical rotation c=2.00, water, 20.0° C., +17.1°.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A process of making dexamphetamine, said process comprising:
   providing a compound of Formula 5 having a regioisomeric purity >99%:

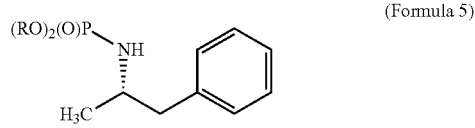

(Formula 5)

wherein R is alkyl or aryl; and
   deprotecting the compound of Formula 5 under acidic conditions effective to produce dexamphetamine of Formula 1:

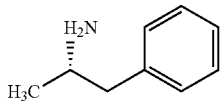

(Formula 1)

wherein the step of providing a compound of Formula 5 comprises the steps of: providing a compound of Formula 4:

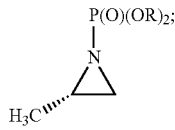

(Formula 4)

wherein R is alkyl or aryl and
   reacting the compound of Formula 4 with phenylmagnesium halide and a copper catalyst under solvent and temperature conditions effective to produce a compound of Formula 5 having a regioisomeric purity >99%,
   wherein the solvent conditions comprise a crystallization step requiring a mixture of two or more solvents, wherein one of the two or more solvents is residue THF.

2. The process according to claim 1 wherein the acidic conditions are aqueous hydrochloric, sulfuric or phosphoric acids.

3. The process according to claim 2 wherein the aqueous acid water content is in an amount of 50% to 90%.

4. The process according to claim 1 wherein R=methyl, ethyl, isopropyl or phenyl.

5. The process according to claim 1 wherein the copper catalyst is CuCl, CuCl$_2$, CuBr CuF, Cu(OAc)$_2$, Cu(acac)$_2$, Cu(OMe)$_2$, Copper turnings or Copper nanoparticles.

6. The process according to claim 1 wherein one of the mixture of two or more solvents is selected from the group consisting of heptanes, an organic ether, 2-methyltetrahydrofuran, and toluene.

7. The process according to claim 1 wherein said temperature conditions range from 25° C. to 80° C.

8. The process according to claim 1, wherein said providing a compound of Formula 4 comprises: providing a compound of Formula 3

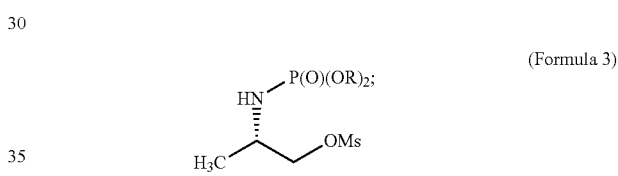

(Formula 3)

wherein R is alkyl or aryl; and
   reacting the compound of Formula 3 with a base under conditions effective to produce a compound of Formula 4.

9. The process according to claim 8 wherein the R=methyl, ethyl, isopropyl or phenyl.

10. The process according to claim 8, wherein the base is potassium hydroxide or potassium carbonate.

11. The process according to claim 8, wherein the step of providing a compound of Formula 3 comprises the steps of: providing a compound of Formula 2

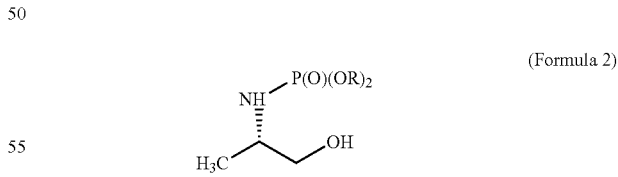

(Formula 2)

wherein R is alkyl or aryl; and
   reacting the compound of Formula 2 with methanesulfonyl chloride and a base under conditions effective to produce a compound of Formula 3.

12. The process according to claim 11 wherein the R=methyl, ethyl, isopropyl or phenyl.

13. The process according to claim 11, wherein said providing a compound of Formula 2 comprises: providing a compound of Formula 1

31

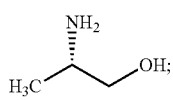
(Formula 1)

and
reacting the compound of Formula 1 with

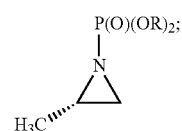

wherein R=alkyl or aryl
under conditions effective to produce a compound of Formula 2.

14. The process according to claim 13 wherein the R=methyl, ethyl, isopropyl or phenyl.

15. The process according to claim 1 wherein said temperature conditions range from 30° C. to 60° C.

16. The process according to claim 1 wherein said temperature conditions range from 40° C. to 52° C.

17. A process of making dex-N-methylamphetamine, said process comprising:
providing a compound of formula 8:

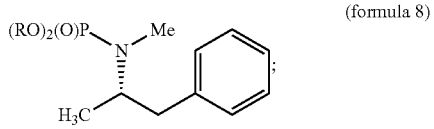
(formula 8)

wherein R is ethyl; and
deprotecting the compound of formula 8 under acidic conditions effective to produce dex-N-methylamphetamine of formula 9:

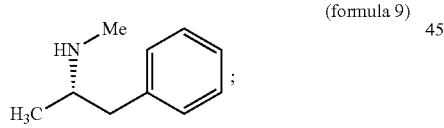
(formula 9)

wherein the step of providing a compound of formula 8 comprises the step of:
providing a compound of formula 5 having a regioisomeric purity >99%:

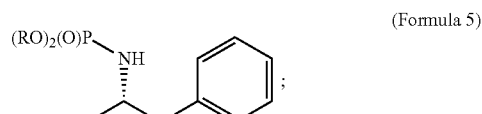
(Formula 5)

wherein R is ethyl; and
reacting the compound of Formula 5 with a methyl alkylating agent and a base to produce the compound of Formula 8;

32 wherein the step of providing a compound of Formula 5 comprises the step of:
providing a compound of formula 4:

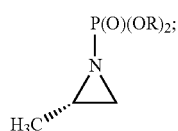
(Formula 4)

wherein R is ethyl; and
reacting the compound of Formula 4 with phenylmagnesium halide and a copper catalyst under solvent and temperature conditions effective to produce a compound of Formula 5 having a regioisomeric purity >99%, wherein the solvent conditions comprise a crystallization step requiring a mixture of two or more solvents, wherein one of the two or more solvent is residue THF.

18. A process of making dex-N-ethylamphetamine, said process comprising:
providing a compound of formula 10:

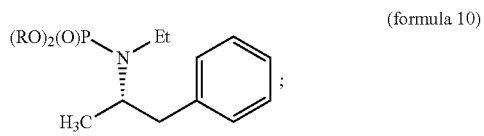
(formula 10)

wherein R is ethyl; and
deprotecting the compound of formula 10 under acidic conditions effective to produce dex-N-ethylamphetamine of formula 11:

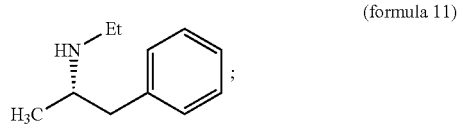
(formula 11)

wherein the step of providing a compound of formula 8 comprises the step of:
providing a compound of formula 5 having a regioisomeric purity >99%:

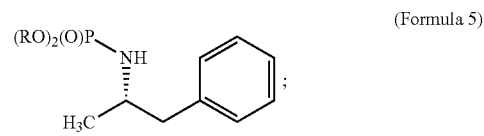
(Formula 5)

wherein R is ethyl; and
reacting the compound of Formula 5 with an ethyl alkylating agent and a base to produce the compound of Formula 8;

wherein the step of providing a compound of Formula 5 comprises the step of:

providing a compound of formula 4:

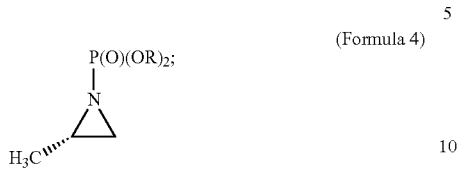

(Formula 4)

wherein R is ethyl; and reacting the compound of Formula 4 with phenylmagnesium halide and a copper catalyst under solvent and temperature conditions effective to produce a compound of Formula 5 having a regioisomeric purity >99%, wherein the solvent conditions comprise a crystallization step requiring a mixture of two or more solvents, wherein one of the two or more solvent is residue THF.

19. The process according to claim 17 wherein the acidic conditions are aqueous hydrochloric, sulfuric or phosphoric acids.

20. The process according to claim 18, wherein the acidic conditions are aqueous hydrochloric, sulfuric or phosphoric acids.

* * * * *